United States Patent [19]
Willems et al.

[11] Patent Number: 6,009,756
[45] Date of Patent: Jan. 4, 2000

[54] DEVICE FOR TESTING FERROMAGNETIC MATERIALS

[75] Inventors: Herbert Willems, Nalbach; Otto-Alfred Barbian, Blieskastel-Ballweiler; Gerhard Hübschen, Saarlouis, all of Germany

[73] Assignees: Pipetronix BmbH, Stutensee; Fraunhofer- Esellschaft Zur Forderung Der Angewandten Forschung, Munich, both of Germany

[21] Appl. No.: 08/860,968

[22] PCT Filed: Nov. 19, 1996

[86] PCT No.: PCT/EP96/05095

§ 371 Date: Jul. 11, 1997

§ 102(e) Date: Jul. 11, 1997

[87] PCT Pub. No.: WO97/19346

PCT Pub. Date: May 29, 1997

[30] Foreign Application Priority Data

Nov. 22, 1995 [DE] Germany .................. 195 43 481

[51] Int. Cl.⁷ .................................................. G01N 29/04
[52] U.S. Cl. .................. 73/643; 73/592; 73/622; 73/625; 73/628
[58] Field of Search ............... 73/643, 598, 600, 73/622, 623, 592

[56] References Cited

U.S. PATENT DOCUMENTS

| | | | |
|---|---|---|---|
| 3,850,028 | 11/1974 | Thompson et al. | 73/643 |
| 4,100,809 | 7/1978 | Bobrov et al. | 73/643 |
| 4,184,374 | 1/1980 | Thompson et al. | 73/643 |
| 4,522,071 | 6/1985 | Thompson | 73/643 |
| 4,727,321 | 2/1988 | Hüschelrath | 73/643 |

FOREIGN PATENT DOCUMENTS

| | | |
|---|---|---|
| 440317 | 8/1991 | European Pat. Off. . |
| 4228426 | 3/1994 | Germany . |

*Primary Examiner*—Hezron Williams
*Assistant Examiner*—Nashmiya Fayyaz
*Attorney, Agent, or Firm*—Antonelli, Terry, Stout & Kraus, LLP

[57] ABSTRACT

Device for testing ferromagnetic materials, such as pipelines and the like, for faults, cracks, corrosion, etc. An one electromagnetic ultrasonic transducer includes at least one high frequency current coil and an arraay of permanent magnets which create a magnetic field for exciting and/or detecting ultrasonic waves in the wall of the ferromagnetic material. The ultrasonic transducer is located between the pole pieces of an additional magnet arrangement that produces a magnetic prefield in the material wall.

39 Claims, 6 Drawing Sheets

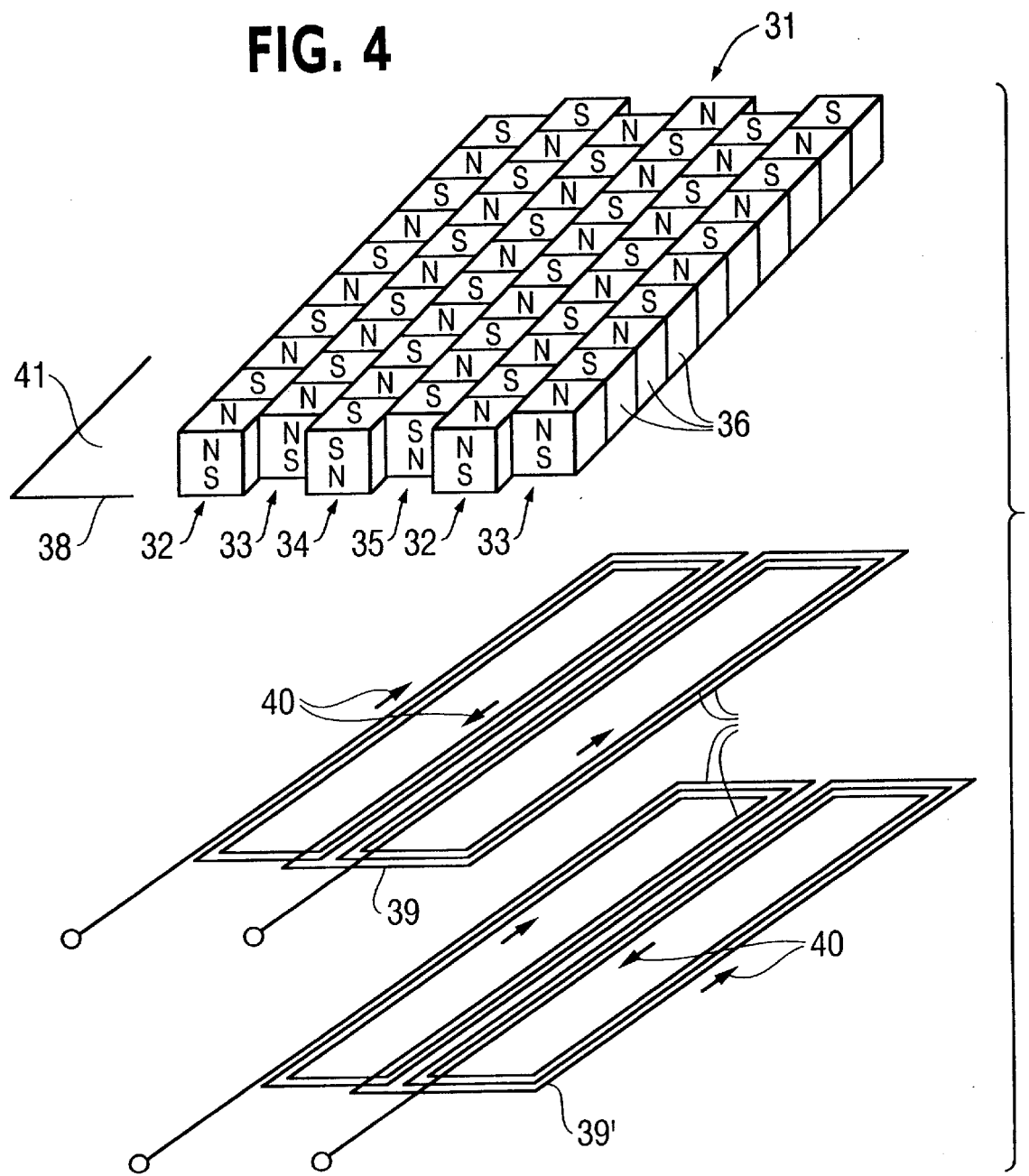

69 µs

DEVICE FOR TESTING FERROMAGNETIC MATERIALS

BACKGROUND OF THE INVENTION

The invention relates to a device for testing ferromagnetic materials, such as pipelines and the like, for faults, cracks, corrosion, etc., using at least one electromagnetic ultrasonic transducer with at least one high frequency current coil in connection with a magnetic field for exciting and/or detecting ultrasonic waves in the material wall, and at least one magnet system producing the magnetic field.

Non-destructive material testing can take place employing ultrasonics, where piezoelectric transducers are used, from which are emitted ultrasonic waves and by means of a coupling medium, such as e.g. water, the waves; are introduced into the workpiece. For the ultrasonic testing of gas pipelines for e.g. crack-like faults on the outside of the pipe, it is only possible to have a dry coupling to the inside of the pipe, e.g. employing airborne noise, ultrasonic excitation by means of a laser, or electromagnetic ultrasonic excitation.

DE-OS 35 11 076 e.g. discloses a test scraper or go-devil for the non-destructive testing and monitoring of pipeline walls made from ferromagnetic material, in which for the detection of wall weaknesses due to corrosion from the outside or inside, a magnetic field, produced there by one of the stray field measuring systems, is used for the electrodynamic excitation of ultrasonics and stray flux measurement. A scraper is provided with uniformly circumferentially distributed electromagnets, which in each case have two aligned measuring heads, a yoke connecting said measuring heads and a magnetic coil on said measuring heads. The field of each electromagnet is parallel to the pipe centre axis. For ultrasonic measurement purposes an air coil is placed directly on at least one of the poles or measuring heads, which is subject to the action of strong and very steep-sided current pulses. The running time of the ultrasonic waves produced by these current pulses, together with the magnetic field in the material acting in the material wall area, is determined and evaluated. It is disadvantageous when using such a testing scraper that Barkhausen noise occurs on moving the measuring head provided with the high frequency coil. This noise is produced in that the ferromagnetic domains in the ferromagnetic material during the movement suddenly reverse to a new equilibrium position as a result of a strong change in the magnetic field. Consequently a current is induced, which can be heard as clicking with an amplifier and a loudspeaker. In the case of rapidly succeeding field changes there is a crackling noise. Therefore the signal-to-noise ratio is inadequate to allow a reliable measurement to take place.

In other known electromagnetic ultrasonic transducers used for the ultrasonic testing and material characterization of electrically conductive materials, e.g. those described in EP-A-609 754, there are at least two rows of permanent magnets with alternating pole distribution and a HF coil positioned below the same for exciting horizontally polarized transverse waves (SH-waves). Also with these ultrasonic transducers, in the dynamic testing of ferromagnetic materials there is an increased background noise, i.e. a reduction of the usable dynamic range, because during the movement of the electromagnetic ultrasonic transducer over a ferromagnetic component Barkhausen noise occurs due to the continuous turn around/magnetic reversal of the magnetic moments within the individual domains of the material. The level of this noise, as a function of the scanning rate, is up to 25 dB.

SUMMARY OF THE INVENTION

Thus, whilst avoiding the aforementioned disadvantages, the problem of the invention is to provide a device of the aforementioned type, by means of which when the electromagnetic ultrasonic transducer is moved over ferromagnetic materials the Barkhausen noise can be suppressed to such an extent that an adequate signal-to-noise ratio (S/N ratio) is obtained.

According to the invention the set problem is solved by a device for testing ferromagnetic materials of the aforementioned type, in that the ultrasonic transducer is placed between pole areas or pieces of an additional, pregmagnetizing magnet arrangement producing a magnetic prefield in the material wall. Thus, the ultrasonic transducer, which in any case ensures an ultrasonic excitation in the material to be tested, is now surrounded by a magnet arrangement in such a way that the material wall, when the ultrasonic transducer is moved over the latter, is so premagnetized in the area to be tested prior to transducer arrival that in said area there is no longer a magnetic reversal or turn around of the moments through the action of the ultrasonic transducer. As a result of this inventive arrangement there is a horizontal, homogeneous premagnetization of the material wall to be tested. As the material wall, through the use of the additional prefield magnetization unit, is magnetized prior to the arrival of the ultrasonic transducer in the particular area close to magnetic saturation, the ultrasonic transducer does not induce such a strong change of the magnetic field in the material wall that on moving said transducer the magnetic moments are reversed, i.e. turned around within the individual domains, so as to then produce a current causing Barkhausen noise.

If the magnet arrangement for prefield magnetization is a unit formed by alternating current magnets, it is ensured that the high frequency transmission pulse is released in accordance with the alternating, horizontal magnetizing field for prefield magnetization in the range of the maximum magnetization field strengths. In the range of the maximum magnetization field strengths for prefield magnetization the Barkhausen noise is at a minimum, because the strongest noise is present in the range of the zero passages of the alternating current in the magnet arrangement for prefield magnetization. Thus, it is possible to measure with a corresponding, adequate signal-to-noise ratio.

In order to, on the one hand, economize the energy supply for said magnet arrangement of alternating current magnets and, on the other hand avoid the complicated triggering of the complete system, preferably the additional magnet arrangement is formed by at least one permanent magnet having at least two pole pieces of different polarity. As a result of such an adequately strong permanent magnet it is possible to produce a static, horizontal, magnetic prefield, and as a result of the magnetization to the vicinity of magnetic saturation, the occurrence of Barkhausen noise is reliably suppressed. As there are now no measurement gaps, as is the case when using alternating current magnets, it is possible to work with a high scanning rate of 1 to 2 m/sec. This is impossible with conventional ultrasonic transducers without the prefield magnetization according to the invention.

Due to the fact that the ultrasonic transducer is preferably centrally positioned between the pole pieces of the additional magnet arrangement, during the testing by ultrasonic excitation it is always in the homogeneous area of the prefield, so as to reliably exclude an action on the moments in the material wall. The ultrasonic transducer is used solely for ultrasonic excitation and for ultrasonic reception and the additional magnet arrangement is solely used for prefield magnetization in the material wall.

Preferably, the ultrasonic transducer is used for exciting/producing horizontally polarized transverse waves, i.e. so-called SH waves in the material to be tested. As opposed to vertically polarized transverse waves (SV waves), such horizontally polarized transverse waves have the advantage that the first mode of the SH waves has no dispersion, i.e. does not react to greater wall thicknesses and less to coatings of the material to be tested. If the SV waves are used for testing thick workpieces, such as pipelines having a thickness between 6 and 20 mm, different Lamb modes are excited, all of which are strongly dispersive, so that there is not an adequately large range. As in particular gas pipelines are coated with bitumen for insulation purposes, the use of vertically polarized transverse waves would have a negative effect. In addition, on reflecting so waves there is no mode conversion at the interface, whereas this does occur with SV w aves. In particular, the normal component of the SV waves in the case of a water environment can be coupled into the latter, which would falsify the measured result.

If the device for testing gas pipelines by ultrasonics according to the invention is e.g. to be used in connection with crack-like faults on the outside of the pipe, preferably electromagnetic ultrasonic transducers are positioned between the pole areas or pieces of a magnetization/measuring unit for stray flux measurement. Such magnet systems for stray flux measurement are e.g. known from DE-OS 35 11 076 as components of test scrapers. However, hitherto high frequency current coils have been placed on one of the pole pieces for producing ultrasonic waves. This then led to the aforementioned disadvantages. According to the inventive device, the electromagnetic ultrasonic transducer is placed in the axial or circumferential direction of the pipe wall to be tested between the poles of different polarity of the stray flux magnet system, so as to permit in a surprisingly simple and space-saving manner an ultrasonic measurement, whilst simultaneously suppressing the Barkhausen noise. The necessary horizontal, static, magnetic prefield is produced by stray flux magnet systems already located on the test scraper. Horizontal means that the prefield runs substantially parallel to the pipe wall in the axial and circumferential directions.

Preferably the static premagnetization of the material wall produced by the pole pieces of different polarity of the additional magnet arrangement is used for setting the operating point of the electromagnetic ultrasonic transducer.

Preferably the pole areas or pieces of different polarity of the additional magnet arrangement receiving the electromagnetic ultrasonic transducer between them are positioned axially parallel to the material to be tested, particularly a pipeline or the like. Such magnet systems, preferably apart from static premagnetization or renewing a prefield, are simultaneously used for detecting, by means of corresponding sensors, a stray field resulting from cracks or openings occurring transversely or in sloping manner to the pipe axial direction. However, it is also simultaneously possible to provide the electromagnetic ultrasonic transducer between two pole pieces or areas of different polarity of an additional magnet arrangement or a stray flux magnet system located in the circumferential direction of the material to be tested, particularly a pipeline, etc. Through such magnet systems, longitudinal cracks in the pipelines or material wall are detected, with simultaneous static premagnetization. For electromagnetic ultrasonic excitation in the material wall, whilst simultaneously suppressing Barkhausen noise, it is merely necessary for there to be a premagnetization of the material walls to be tested through a static, horizontal, magnetic prefield. It is unimportant for the measurement whether this takes place in the axial or circumferential direction.

In a further preferred development, the electromagnetic ultrasonic transducers are so positioned with respect to the magnetic field direction of the prefield between the pole pieces of different polarity of the additional magnet system that their emission or irradiation direction is perpendicular or parallel to the field direction of the prefield. This is possible in that the excitation of the horizontally polarized transverse waves in the wall to be tested takes place solely through the ultrasonic transducers, and not by a combination a high frequency coil with e.g. a stray flux magnetization/measuring unit. The additional magnet arrangement is exclusively used for producing the strong static, horizontal, magnetic prefield necessary for Barkhausen noise suppression as well as in the case of a stray flux unit for detecting longitudinally and axially directed cracks by measuring the exiting stray field.

The high frequency coils of the electromagnetic ultrasonic transducer can be air coils, which are preferably constructed as flat coils with meandering windings.

The electromagnetic magnetic ultrasonic transducer for exciting and receiving horizontally polarized transverse waves (SH waves) is preferably formed by an arrangement of permanent magnet segments with alternating pole distribution and at least one HF coil positioned below the permanent magnet segments. In this case the excitation of horizontally polarized transverse waves in the material wall to be tested takes place solely through the electromagnetic ultrasonic transducers. When using a sequence of permanent magnet segments of alternating pole distribution and a HF coil positioned below the same for exciting SH waves, the action area of the magnetic fields produced by the small permanent magnets is limited to the direct area below the magnets, i.e. the HF coil and essentially the surface of the wall to be tested, so that these fields in no way counteract the strong premagnetization field, i.e. there can be no magnetic reversal processes in the wall, and consequently the Barkhausen noise is reliably suppressed. This structure of an electromagnetic ultrasonic transducer, compared with a high frequency coil placed between the pole pieces of a U-shaped magnet, has the advantage that on exciting SH waves in the material there is not merely a purely magnetostrictive excitation of these SH waves. Magnetostrictive excitation is to a certain extent dependent on the material characteristics, so that the excitation thereof must be precisely controlled with high effort and cost in order not to obtain falsified signals. Ultrasonic transducers formed by an arrangement of permanent magnet segments of alternating pole distribution and at least one HF coil below them could hitherto only be used for the static testing of ferromagnetic workpieces and walls, because in particular in the case of a rapid movement over the workpiece to be tested, the already described Barkhausen noise occurred.

According to a further development, the electromagnetic ultrasonic transducer has an arrangement of two rows of permanent magnets of alternating pole distribution and onto which is wound a rectangular coil. Preferably the high frequency coil is so positioned below the rows of permanent magnets of alternating pole distribution that in each case high frequency coil elements with the same current direction are associated with permanent magnet rows with the same polarity sequence. The supply of high frequency currents to such a high frequency or rectangular coil then gives rise to eddy current in the ferromagnetic material under test, and the pattern thereof substantially corresponds to that of the current of the high frequency coil. Due to the interaction between these eddy current and the magnetic fields produced by the permanent magnet segments, in the material Lorentz forces directly occur perpendicular to the eddy currents and to the magnetic field applied. Due to the fact that adjacent segments of a row of permanent magnet segments have different polarities, in this way shear forces of alternating direction are produced, which lead to the excitation of SH waves in the material. As the thus acting forces are in the same direction due to the orientation and arrangement of the high frequency coil below the rows of adjacent permanent segment rows, via the Lorentz forces there can be an optimum particle deflection in the ferromagnetic material, which then leads to a direct excitation of ultrasonic waves with a bidirectional directional characteristic, which is symmetrically oriented with respect to the transducer center. Unlike in the case of a magnetostrictive excitation of ultrasonic waves, in the case of such an excitation via Lorentz forces there is no dependence with respect to the materials used, so that the disadvantages occurring with magnetostrictive excitation no longer arise. As now use is made of an array of permanent magnet segments with high frequency coil elements placed under each segment sequence of a magnet, horizontally polarized transverse waves are "emitted" on either side of the electromagnetic ultrasonic transducer, so that an association of individual signals with an emission direction, i.e. a clearly defined location of a material fault in the case of fixed position of the electromagnetic ultrasonic transducer is not possible.

Thus, in another embodiment, the electromagnetic ultrasonic transducer comprises at least two sets of orientation-chessboard pattern-like distributed permanent magnets of different polarity with high frequency coil elements located below them. Thus, in this embodiment the complete ultrasonic transducer is subdivided into individual sets of magnet segments and high frequency coil segments, which are preferably supplied with signals in time-delayed manner. These transducers operate according to the phased array principle. This is based on the principle of superimposing individual waves to form a resultant wave, i.e. the superimposing of the individual waves produced by the different transducer coils as a resultant wave produces the desired type of ultrasonic wave. Through the emission and reception of ultrasonic waves by means of several transmitters and receivers with planned phase-displaced excitation of the transducers, it is ensured that with a precisely tuned phase delay there is a planned constructive and destructive interference. As a result of this preferred embodiment the desired front to back ratio can be set.

In another embodiment, the electromagnetic ultrasonic transducer has an arrangement of at least four rows of permanent magnet segments of alternating polarity, and each pair of two adjacent rows of segments is displaced by a quarter of the periodicity of the individual permanent magnets of each row along their longitudinal axis, and an individual high frequency coil is provided for each adjacent permanent magnet arrangement. As the two high frequency coils can be supplied with signals phase-delayed by 90°, it is possible to bring about a unilateral, high quality directional characteristic of the horizontally polarized transverse waves produced by Lorentz forces, with an excellent suppression of parasitic sound waves in the ferromagnetic material to be tested. The two bidirectionally emitted waves constructionally interfere in one direction and cancel one another out in the other direction. This makes it possible to obtain the desired front to back ratio, and this is helped by the fact that the two high frequency coils are nested.

Whereas in the preceding embodiments air coils are always used, which are placed below permanent magnet segments of alternating polarity, according to a further embodiment use is made of a high frequency coil wound onto a magnetically conductive core. The core is preferably a ring band core, which partly surrounds an arrangement of several rows of permanent magnets of alternating pole distribution. In this embodiment the eddy currents necessary for sound excitation are indirectly coupled into the material surface by the impression of dynamic high frequency magnetic fields.

Thus, a device for the electromagnetic testing of ferromagnetic materials is created by means of which, when using electromagnetic ultrasonic transducers for horizontally polarized transverse waves on ferromagnetic components when moving ultrasonic transducers over the testpiece to be tested, the hitherto occurring Barkhausen noise is reliably suppressed and a high S/N ratio is obtained.

Other advantages and features of the invention can be gathered from the claims and the following description of embodiments, with reference to the attached drawings, wherein;

FIG. 4 depicts an electromagnetic ultrasonic transducer for transverse waves polarized perpendicular to the plane of incidence with a unilateral directional characteristic in an exploded view.

Figure 1:
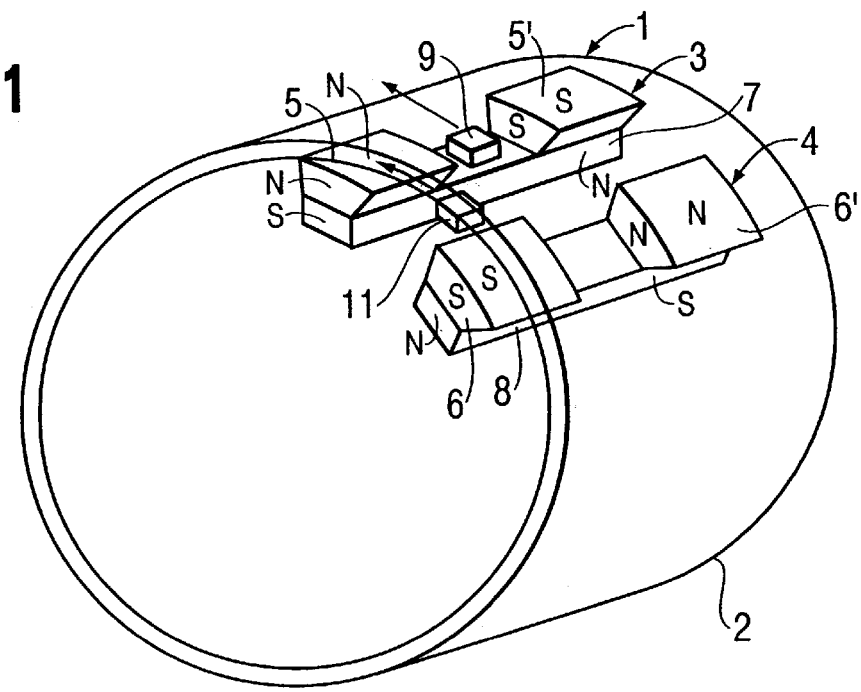
FIG. 1 is a diagrammatic representation of the inventive arrangement of electromagnetic ultrasonic transducers between the pole pieces of a stray flux magnetizing unit within a pipeline to be tested.
Figure 7:
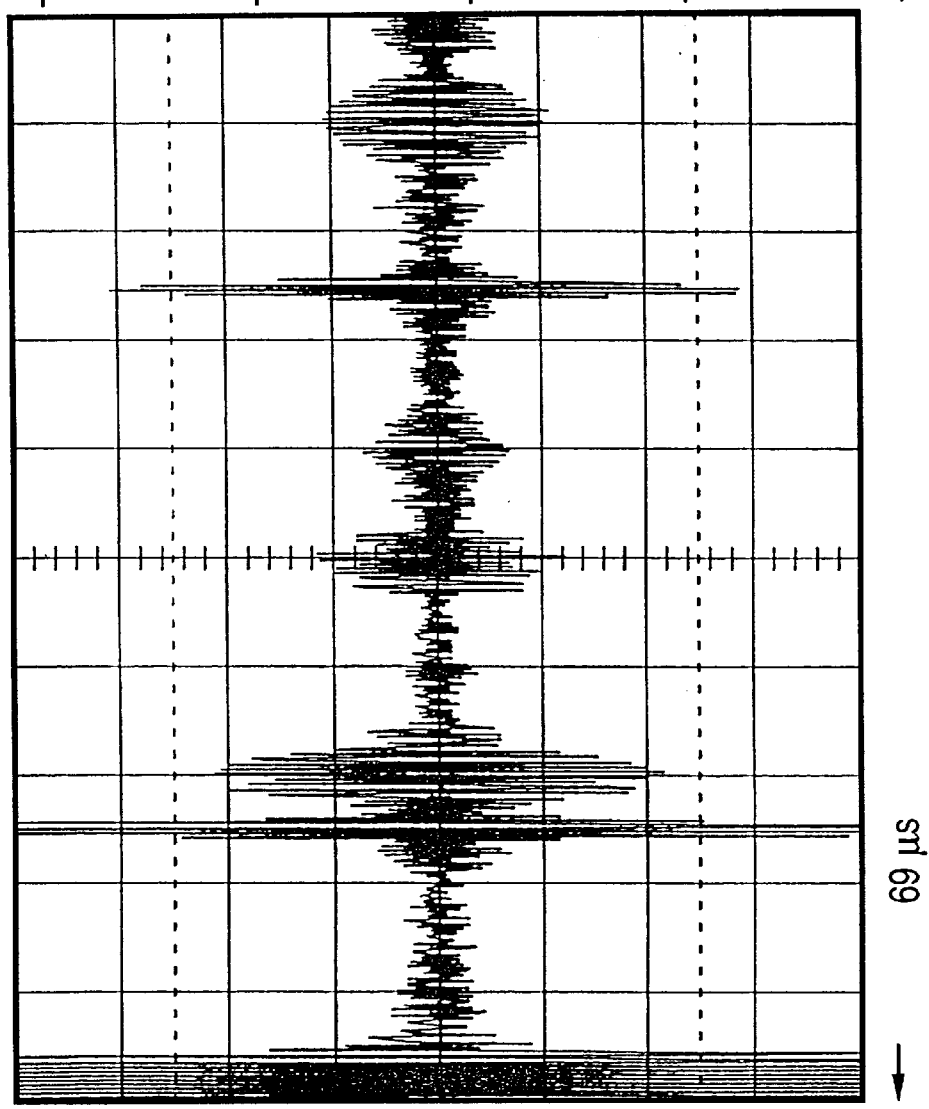

FIG. 7 illustrates the measuring signal of an electoromagnetic ultrasonic, according to the invention. transducer with an arrangement The inventive device 1 diagrammatically and partly shown in FIG. 1 in the represented embodiment is located within an also only partly shown pipeline having a wall 2. The device 1 has two stray flux magnetizing units 3, 4 in the form of U-shaped permanent magnets, with in each case two pole pieces 5, 5', 6, 6' in axially parallel alignment with one another and interconnected by means of a yoke 7, 8. Centrally between the pole pieces 5, 5' of the magnetizing unit 3 is provided, in the horizontally directed static magnetic field between said pole pieces 5, 5', an electromagnetic ultrasonic transducer 9 (EMUS transducer), which in the represented embodiment has an emission direction perpendicular to the magnetic field direction of the static prefield produced by the magnetizing unit 3 for ultrasonic excitation in the material wall 2. A more detailed description will be given hereinafter of excitation in a ferromagnetic material, such as a pipe wall or the like. For illustration purposes, between the pole pieces 5, 6' of the magnetizing units 3, 4, a further transducer 11 is placed circumferentially and centrally between said pole pieces 5, 6' and has an emission direction parallel to the magnetic field direction of the static prefield. The emission direction of each transducer 9, 11 is independent of the static prefield of the permanent magnets 3, 4 used for the premagnetization of the wall 2, because the ultrasonic excitation in the material wall 2 to be tested solely takes place through the ultrasonic transducers 9, 11, and consequently the stray flux magnetizing units 3, 4 are used solely for the premagnetization of the wall 2 and for stray flux measurement.

In the embodiment shown in FIG. 2 the ultrasonic transducer 17 for exciting horizontally polarized transverse waves has a magnet arrangement formed from two rows 18, 18 ' of periodically arranged permanent magnets 19 or permanent magnet systems 19 of alternating polarity, on which is placed a rectangular coil 20 which is shown in the exploded view below the magnet arrangement. The supply of high frequency current to the rectangular coil 20 and, in a direction indicated at a fixed time with the arrows 21, then produces in electrically conductive materials, such as a pipe wall, by means of Lorentz forces a particle deflection, which leads to a direct excitation of ultrasonic waves of the aforementioned type. As can be gathered from FIG. 2, the segments of the high frequency coil 20 are so positioned below the individual rows 18, 18' that the currents 21 in the high frequency coils 20 are always in the same direction in a first row 18 and in the opposite direction in the neighbouring second row 18'. As a result of the current pulses, in the material to be tested are produced eddy currents with a pattern corresponding to the high frequency coil currents, so that by interaction between said eddy currents and the magnetic field produced by the permanent magnets 19, Lorentz forces act perpendicular to the eddy field produced and to the magnetic field direction in the material. As the polarity of the neighbouring permanent magnets 19', 19" of the two rows is in opposition, but simultaneously the current pulses in said two rows are in opposition, the forces acting below the permanent magnets 19', 19" are in the same direction, but in the opposite direction to the forces of a row of adjacent permanent magnets 19. Thus, the desired horizontally polarized transverse wave can be excited. The thus produced ultrasonic waves have a bilateral directional characteristic, which is symmetrically oriented with respect to the transducer centre. This transducer centre is by means of the plane of symmetry given the reference 22. As the ultrasonic waves produced are "emitted" to either side symmetrically with respect to the transducer centre 22, an evaluation of the reception signals is made more difficult, because there can be no association of individual signals with an emission direction in the case of a fixed position of the ultrasonic transducer 17. Correspondingly, no clear location of a material fault is possible solely through the movement of the electromagnetic ultrasonic transducer.

Figure 3:
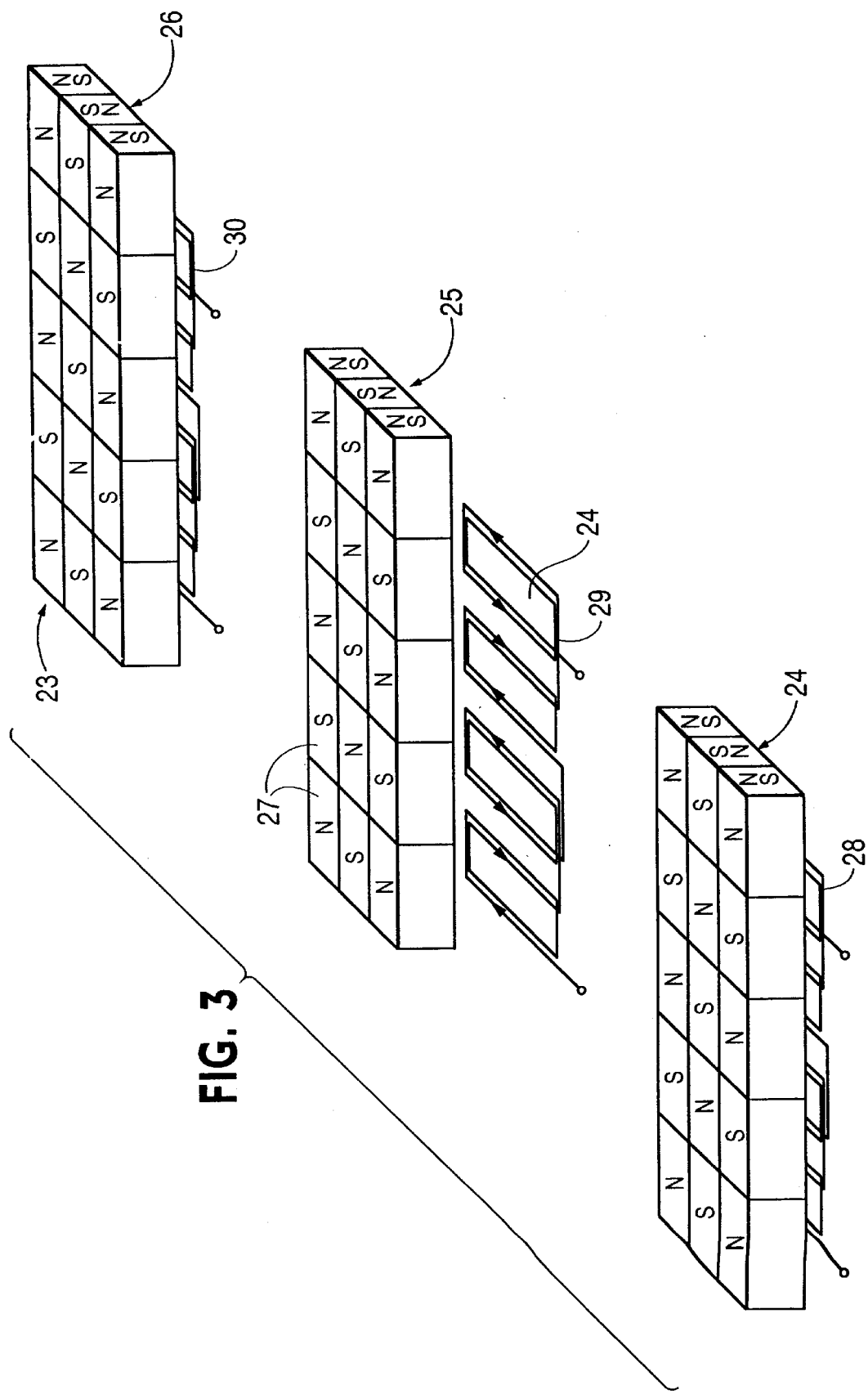
FIG. 3 depicts an electromagnetic ultrasonic transducer with three sets of permanent magnet segments, with high frequency coils below the same in an exploded view.

In the embodiment of FIG. 3, the electromagnetic ultrasonic transducer 23 for exciting horizontally polarized transverse waves (SH waves) has three sets 24, 25, 26 of permanent magnets 27 distributed in chessboard pattern in their orientation, with high frequency coil elements 28, 29, 30 positioned below them. Such an EMUS transducer can contain up to eight sets of permanent magnet arrangements. In the represented embodiment, the high frequency coils 28, 29, 30 have a quadruple meander-like loop formation and are located below the 5×3 arrays of permanent magnets 27. The high frequency coils 28, 29, 30 of said electromagnetic ultrasonic transducer 23 are in each case activated in a time-delayed manner, their current direction being indicated by arrows. The distribution of the high frequency coil elements/segments 28, 29, 30 takes place below the rows in the same way as in the preceding embodiment, so that a further description is unnecessary here. As a result of the time-delayed activation of the HF coils, it is possible to set a front to back ratio unlike in the preceding embodiment.

In the embodiment shown in FIG. 4, the electromagnetic ultrasonic transducer 31 for exciting Sli waves has six rows 32, 33, 34, 35 of periodically arranged permanent magnets 36. In each case adjacent rows 32 and 33 or 32 and 35 or 35 and 34, as well as 34 and 33 are mutually displaced by half the width of a single permanent magnet 36. As can be seen in FIG. 4, the first and second rows 32, 33 in this embodiment are repeated after precisely four rows.

A double rectangular coil 39 is so fitted to the two permanent magnet arrangements formed by the three rows 33 and 35, whose individual permanent magnets 36 are at the same height with respect to a base line but have different polarities, in such a way that the current direction 40 alternates between individual rows. On the remaining three rows 32 and 34 in this embodiment is fitted a second double rectangular coil 39', which is nested with respect to the first coil 39, and, in coil 39' once again the current direction alternates between individual magnet rows. The two high frequency coils 39, 39' are operated during transmission with transmission current signals phase-displaced by 90°.

Once again a unilateral directional characteristic can be obtained through this electromagnetic ultrasonic transducer 31. The size of the magnets and the high frequency is chosen in such a way that the "emission angle" of the ultrasonic signal to be excited in the material grazes the plane 41 on the underside of the permanent magnets 36. Through the spatial displacement by a quarter of a wavelenght of the "ultrasonic sources" that excites the transverse waves, and that comprises permanent magnets and high frequency coils, which displacement is obtained due to the permanent magnet arrangement being displaced relative to the base line 38, in one emission direction there is a phase difference of the signals by 180°, i.e. a cancellation of the signals, and in the other emission direction a constructive superimposing of the signals with a phase difference of 0 or 360°.

Figure 2:
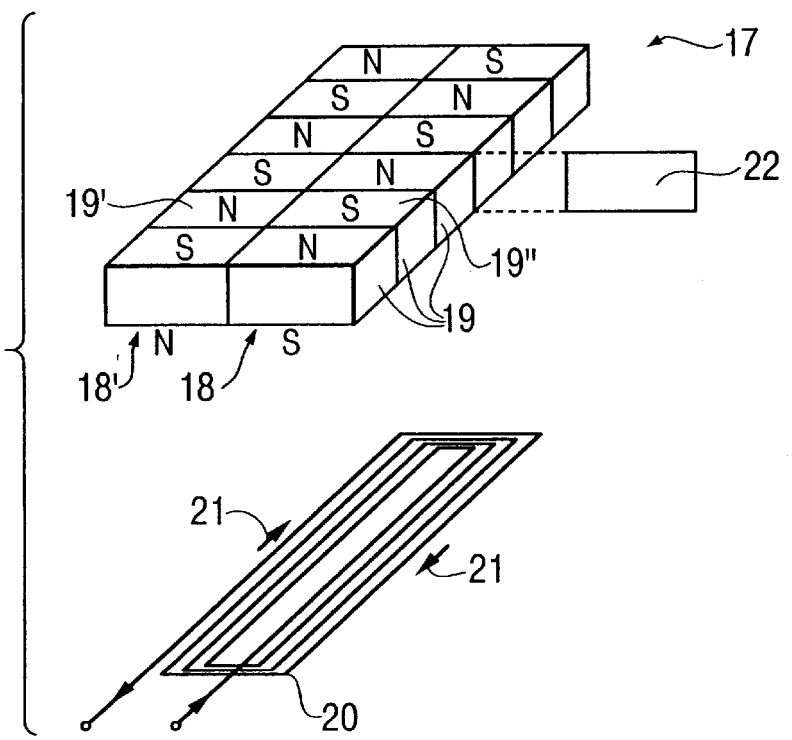
FIG. 2 depicts an ultrasonic transducer in an exploded view, with two rows of permanent magnet segments of alternating pole distribution and a high frequency coil positioned below the same.

It is common to all the electromagnetic ultrasonic transducers for exciting and receiving SH waves shown in FIGS. 2 to 4, that the leads and transition segments of the high frequency current coils are kept as small as possible, so as to ensure an optimum excitation of the horizontally polarized transverse waves by particle deflection using Lorentz forces. In addition, the width of each row of permanent magnet segments of alternating polarity is preferably small compared with the length thereof, so that the transition segments of each high frequency coil can be kept small compared with the length of each row of permanent magnet segments.

Figure 5A:
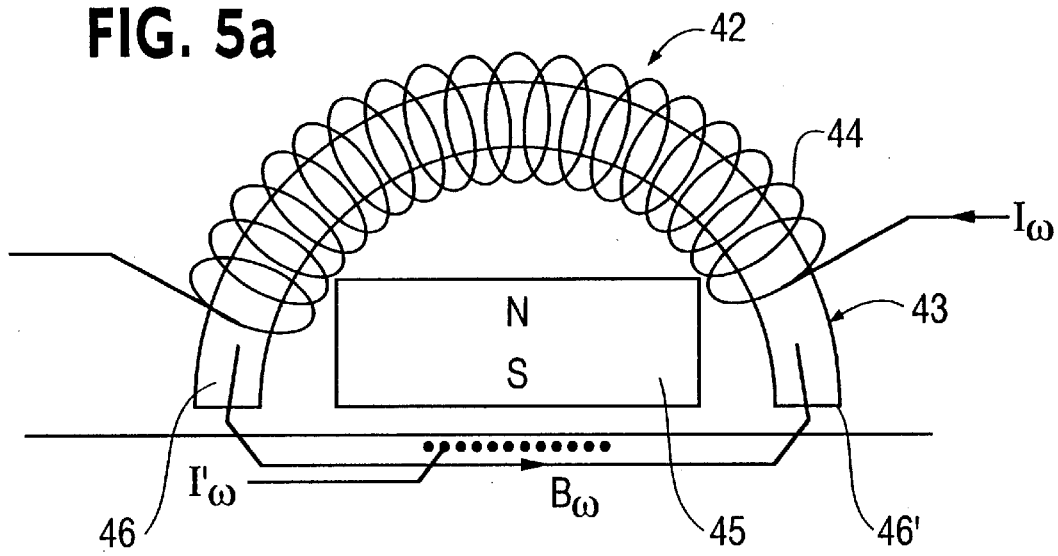
FIG. 5a depicts an electromagnetic ultrasonic transducer with a high frequency coil wound on a ring band core.
Figure 5B:
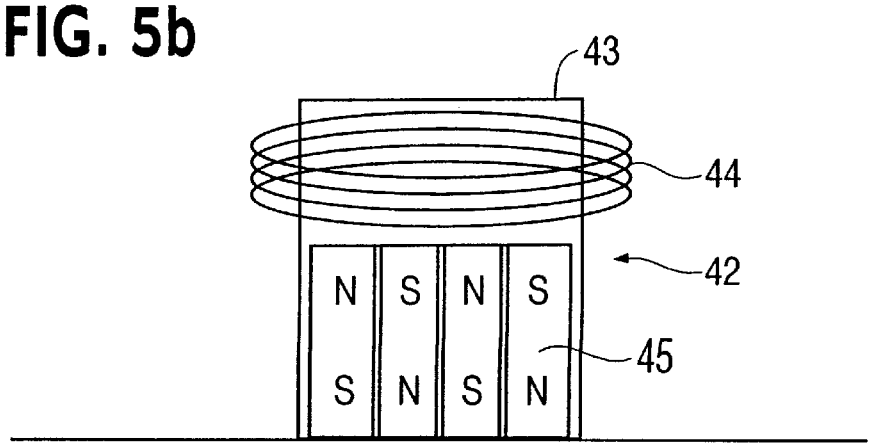
FIG. 5b depicts the transducer of FIG. 5a in side view.

In the last embodiment shown in FIGS. 5a and 5b, the electromagnetic ultrasonic transducer 42 for exciting and receiving SH waves has a high frequency coil 44 wound onto a magnetically conductive ring band core 43. The core 43 is positioned above an arrangement of several rows of permanent magnets 45 of alternating pole distribution and laterally surrounds the same with its legs 46, 46'. In order to excite a horizontally polarized transverse wave, the arrangement is such that the rows of permanent magnets 45 have their long side in the direction of the dynamic B field. By means of said electromagnetic ultrasonic transducer 42, the eddy currents necessary for sound excitation are indirectly coupled into the material surface through the impression of dynamic high frequency magnetic fields.

Figure 6:
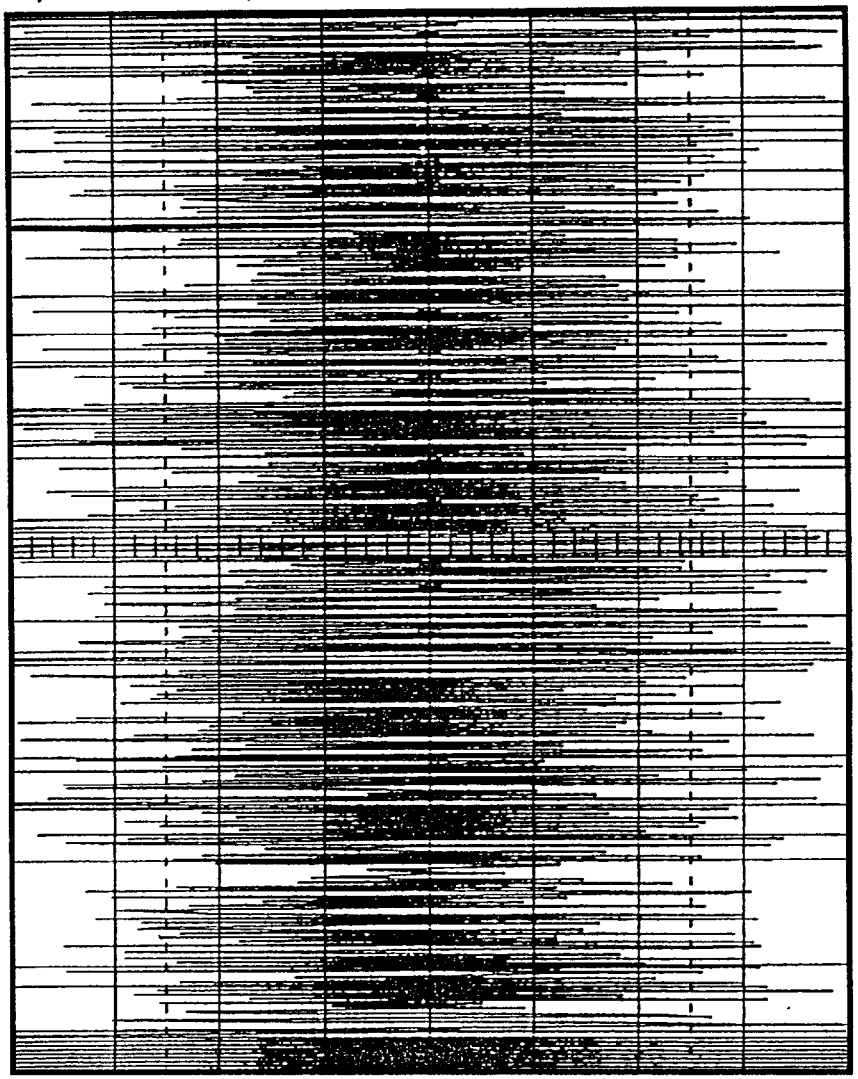
FIG. 6 illustrates the measuring signal of an electromagnetic ultrasonic transducer without the inventive arrangement between the pole pieces of a magnetizing unit.

By means of the electromagnetic ultrasonic transducer shown in FIG. 3 and which, according to the invention, is placed between the pole pieces of an additional magnet arrangement of strong permanent magnets, e.g. a stray flux magnetizing unit, it is possible to obtain a measuring signal in accordance with FIG. 7 with a high S/N ratio. Without the inventive arrangement, due to Barkhausen noise resulting from the ultrasonic transducer of FIG. 3 only a measuring signal as shown in FIG. 6 is obtained.

It is claimed:

1. A device for detecting faults in a ferromagnetic material, said device comprising:

an ultrasonic transducer including a plurality of permanent magnets, each permanent magnet having two poles of different polarity and producing a magnetic field, the plurality of permanent magnets being arranged so that adjacent permanent magnet poles have opposite polarities; and a high frequency current coil adapted to be connected to a high frequency current source to generate a high frequency field, for cooperating with the magnetic fields of the permanent magnets to excite horizontally polarized transverse ultrasonic waves in the ferromagnetic material; and a first premagnetizing magnet adapted to be positioned adjacent a surface of the ferromagnetic material, the first premagnetizing magnet having two pole pieces of different polarities, for producing a premagnetizing magnetic field in the ferromagnetic material, wherein the ultrasonic transducer is positioned between the pole pieces of the first premagnetizing magnet so that the premagnetizing magnetic field of the first premagnetizing magnet suppresses Barkhausen noise in the ferromagnetic material.

2. A device according to claim 1, wherein the premagnetizing magnet is permanent magnet.

3. A device according to claim 1, wherein the ultrasonic transducer is positioned centrally between the pole pieces of the premagnetizin magnet.

4. A device according to claim 1, further comprising:

a second premagnetizing magnet adapted to be positioned adjacent the surface of the ferromagnetic material, the second premagnetizing magnet having two pole pieces of different polarities, for producing a second premagnetizing magnetic field in the ferromagnetic material; and a stray flux measurement unit positioned between the pole pieces of the second premagnetizing magnet.

5. A device according to claim 4, wherein the permanent magnets are positioned in four longitudinal rows of alternating polarity and of regular periodicity, with each pair of adjacent rows being displaced longitudinally by a quarter of the periodicity of the individual permanent magnets of each row, and the high frequency current coil comprises two coil elements, the two coil elements being alternatingly positioned beneath adjacent rows of the permanent magnets.

6. A device according to claim 1, wherein the first premagnetizing magnet produces the premagnetizing magnetic field in the ferromagnetic material at a level sufficient to set an operating point for the ultrasonic transducer.

7. A device according to claim 1, wherein the pole pieces of the premagnetizing magnet are positioned axially parallel to the ferromagnetic material to be tested.

8. A device according to claim 1, wherein the pole pieces of the premagnetizing magnet are positioned circumferentially around the ferromagnetic material.

9. A device according to claim 1, wherein the ultrasonic transducer generates the ultrasonic waves in a direction perpendicular to the field direction of the premagnetizing field produced by the premagnetizing magnet.

10. A device according to claim 1, wherein the ultrasonic transducer generates the ultrasonic waves in a direction parallel to the field direction of the premagnetizing field produced by the premagnetizing magnet.

11. A device according to claim 1, wherein the high frequency current coil is an air coil.

12. A device according to claim 11, wherein the high frequency current coil is a flat coil with meandering windings.

13. A device according to claim 1, wherein the high frequency coil is positioned below the permanent magnets.

14. A device according to claim 13, wherein the permanent magnets are arranged in two rows, and the high frequency current coil is a rectangular coil.

15. A device according to claim 13, wherein the high frequency current coil is positioned such that high frequency coil elements having the same current direction are associated with permanent magnet rows of the same polarity sequence.

16. A device according to claim 1, wherein the permanent magnets are positioned in at least two sets in a chessboard pattern, and the high frequency current coil comprises two coil elements located below the respective sets of permanent magnets.

17. A device according to claim 16, wherein the two coil elements are supplied in time-delayed manner with signals.

18. A device according to claim 13, wherein the permanent magnets are positioned in four longitudinal rows of alternating polarity and of regular periodicity, with each pair of adjacent rows being displaced longitudinally by a quarter of the periodicity of the individual permanent magnets of each row, and the high frequency current coil comprises two coil elements, the two coil elements being alternatingly positioned beneath adjacent rows of the permanent magnets.

19. A device according to claim 18, wherein the two coil elements are supplied with signals phase-displaced by 90°.

20. A device according to claim 18, wherein the two coil elements are nested.

21. A device according to claim 1, wherein the high frequency current coil is wound onto a magnetically conductive core.

22. A device according to claim 21, wherein the core is a ring band core partly surrounding several rows of the permanent magnets.

23. A device according to claim 5, wherein the two coil elements are supplied with signals phase-displaced by 90°.

24. A device according to claim 5, wherein the two coil elements are nested.

25. A device for detecting faults in a ferromagnetic pipe, said device comprising:

an ultrasonic transducer including a plurality of permanent magnets, each permanent magnet having two poles of different polarity and producing a magnetic field, the plurality of permanent magnets being arranged so that adjacent permanent magnet poles have opposite polarities; and a high frequency current coil adapted to be connected to a high frequency current source to generate a high frequency field, for cooperating with the magnetic fields of the permanent magnets to excite horizontally polarized transverse ultrasonic waves in the ferromagnetic pipe; and first and second premagnetizing magnets adapted to be positioned adjacent an inner surface of the ferromagnetic pipe, each premagnetizing magnet having two pole pieces of different polarities, for producing first and second premagnetizing magnetic fields in an axial direction and a circumferential direction, respectively, in a wall of the ferromagnetic pipe, wherein the ultrasonic transducer is positioned between the pole pieces of one of the first and second premagnetizing magnets so that the premagnetizing magnetic field of said one of the first and second premagnetizing magnets suppresses Barkhausen noise in the ferromagnetic pipe.

26. A device according to claim 25, further comprising a stray flux measurement unit positioned between the pole pieces of another one of the first and second premagnetizing magnets.

27. A device according to claim 4, wherein said first premagnetizing magnet produces a premagnetizing magnetic field in the ferromagnetic material sufficient to set an operating point for the ultrasonic transducer.

28. A device according to claim 4, wherein the ultrasonic transducer generates the ultrasonic waves in a direction perpendicular to the field direction of the premagnetizing magnetic field produced by said first premagnetizing magnet.

29. A device according to claim 4, wherein the ultrasonic transducer generates the ultrasonic waves in a direction parallel to the field direction of the premagnetizing magnetic field produced by said first premagnetizing magnet.

30. A device according to claim 4, wherein the high frequency current coil is an air coil.

31. A device according to claim 30, wherein the high frequency current coil is a flat coil with meandering windings.

32. A device according to claim 4, wherein the high frequency coil is positioned below the permanent magnets.

33. A device according to claim 32, wherein the permanent magnets are arranged in two rows, and the high frequency current coil is a rectangular coil.

34. A device according to claim 32, wherein the high frequency current coil is positioned such that high frequency coil elements having the same current direction are associated with permanent magnet rows of the same polarity sequence.

35. A device according to claim 4, wherein the permanent magnets are positioned in two sets in a chessboard pattern, and the high frequency current coil comprises two coil elements located below the permanent magnets.

36. A device according to claim 35, wherein one coil element is beneath each set of permanent magnets, and the two coil elements are supplied in time-delayed manner with signals.

37. A device according to claim 1, wherein the permanent magnets are positioned in four longitudinal rows of alternating polarity and of regular periodicity, with each pair of adjacent rows being displaced longitudinally by a quarter of the periodicity of the individual permanent magnets of each row, and the high frequency current coil comprises two coil elements, the two coil elements being alternatingly positioned beneath adjacent rows of the permanent magnets.

38. A device according to claim 4, wherein the high frequency current coil is wound onto a magnetically conductive core.

39. A device according to claim 38, wherein the core is a ring band core party surronding several rows of the permanent magnets.

* * * * *